(12) United States Patent
Yao et al.

(10) Patent No.: US 9,199,010 B2
(45) Date of Patent: Dec. 1, 2015

(54) WOUND DRAINAGE THERAPY SYSTEM

(71) Applicant: APEX MEDICAL CORP., New Taipei (TW)

(72) Inventors: Nan-Kuang Yao, New Taipei (TW); Luo-Hwa Miao, New Taipei (TW); Jhy-Wen Wu, New Taipei (TW); Yu-Yi Chien, New Taipei (TW); Li-Ling Li, New Taipei (TW); Chih-Tsan Chien, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 387 days.

(21) Appl. No.: 13/685,027

(22) Filed: Nov. 26, 2012

(65) Prior Publication Data

US 2014/0148768 A1    May 29, 2014

(51) Int. Cl.
*A61M 1/00* (2006.01)

(52) U.S. Cl.
CPC ........... *A61M 1/0011* (2013.01); *A61M 1/0023* (2013.01); *A61M 1/0031* (2013.01); *A61M 1/0088* (2013.01)

(58) Field of Classification Search
CPC ............ A61M 1/0011; A61M 1/0023; A61M 1/0088; A61M 1/0031; A61M 1/0209; A61J 1/10; A61J 1/12; A61J 1/0209; A61J 1/2093; A61J 1/1475; A61J 1/1406; A61J 2001/2024; A61J 2001/201; A61B 5/1427; A61B 5/1438; B29L 2031/7148
USPC .................................................. 604/408–410
See application file for complete search history.

(56) References Cited

U.S. PATENT DOCUMENTS

2012/0053541 A1*   3/2012   Yao et al. ...................... 604/319

\* cited by examiner

*Primary Examiner* — Philip R Wiest
*Assistant Examiner* — Ariana Zimbouski
(74) *Attorney, Agent, or Firm* — CKC & Partners Co., Ltd.

(57) ABSTRACT

A wound drainage therapy system includes a wound seal unit, a fluid collector unit, a vacuum driving unit and an actuator. The fluid collector unit is detachably connected with the wound seal unit, and the fluid collector unit has a multiple-pipe integration module and a collection bag. The multiple-pipe integration module has a first row connection port group and a second row connection port group. The vacuum driving unit has a vacuum generator. The actuator has a motor, a negative pressure detector and a positive pressure detector, wherein the motor is used to drive the vacuum generator to operate and the motor is detachably connected with the vacuum generator. A connection port of the negative pressure detector and a connection port of the positive pressure detector are detachably connected with another two connection ports of the second row connection port group respectively.

15 Claims, 11 Drawing Sheets

WOUND DRAINAGE THERAPY SYSTEM

BACKGROUND

1. Field of Invention

The present invention relates to a wound caring device. More particularly, the present invention relates to a negative pressure wound drainage therapy device.

2. Description of Related Art

Negative pressure wound therapy employs a vacuum pump to provide a negative pressure environment for a wound so as to extract wound pus and infected material, to attract the healthy tissue fluid to maintain a moist healing environment, and to promote the surrounding blood microcirculation, thereby accelerating wound healing effect.

In order to cope with the negative pressure wound therapy, there are a lot of negative pressure wound care devices came into being. However, the overall volume of a conventional negative pressure wound care device is too large such that it is not conducive to the patient carries and thus limited to the patients stayed in hospital. In addition, the conventional negative pressure wound care device is equipped with several pipes such that it is prone to the disadvantage of pipe entanglement that also causes the patients inconvenient. For the forgoing reasons, there is a need for further improving the negative pressure wound care device, so that the negative pressure wound therapy can benefit more patients.

SUMMARY

It is therefore an objective of the present invention to provide an improved wound drainage therapy system.

In accordance with the foregoing and other objectives of the present invention, a wound drainage therapy system includes a wound seal unit, a fluid collector unit, a vacuum driving unit and an actuator. The wound seal unit is attached to a wound. The fluid collector unit is detachably connected with the wound seal unit, and the fluid collector unit has a multiple-pipe integration module and a collection bag. The multiple-pipe integration module has a first row connection port group that is connected with the collection bag. The multiple-pipe integration module further has a second row connection port group, and the first row connection port group communicates with the second row connection port group. The vacuum driving unit has a vacuum generator inside thereof, two connection ports of the vacuum generator is detachably connected with two connection ports of the second row connection port group respectively. The actuator has a motor, a negative pressure detector and a positive pressure detector inside thereof, wherein the motor is used to drive the vacuum generator to operate and the motor is detachably connected with the vacuum generator. A connection port of the negative pressure detector and a connection port of the positive pressure detector are detachably connected with another two connection ports of the second row connection port group respectively.

According to another embodiment disclosed herein, the first row connection port group includes first, second and third connection ports, and the second row connection port group includes fourth, fifth, sixth and seventh connection ports.

According to another embodiment disclosed herein, the two connection ports of the vacuum generator are connected with the fourth and fifth connection ports respectively, the connection port of the positive pressure detector is connected with the seventh connection port, and the connection port of the negative pressure detector is connected with the sixth connection port.

According to another embodiment disclosed herein, the first, fourth and seventh connection ports communicate with one another, the second and fifth connection ports communicate with each other, the third and sixth connection ports communicate with each other, and the seventh connection port contains a backwater gate inside to stop flows reversed from the first or fourth connection ports.

According to another embodiment disclosed herein, when the vacuum driving unit is assembled to the actuator, the two connection ports of the vacuum generator, the connection port of the negative pressure detector and the connection port of the positive pressure detector are located on a common flat surface of a combined assembly of the vacuum driving unit and the actuator.

According to another embodiment disclosed herein, the first, second, third, fourth, fifth, sixth and seventh connection ports are located on a common flat surface of the multiple-pipe integration module.

According to another embodiment disclosed herein, the flat surface of the multiple-pipe integration module has two fastening slots.

According to another embodiment disclosed herein, the flat surface of the combined assembly of the vacuum driving unit and the actuator has two fastening hooks that detachably engage with the two fastening slots respectively.

According to another embodiment disclosed herein, the actuator has a concave trough to accommodate the vacuum driving unit and the concave trough has a fastening slot.

According to another embodiment disclosed herein, the vacuum driving unit has a fastening hook that detachably engages with the fastening slot within the concave trough such that the vacuum driving unit is secured within the concave trough of the actuator.

According to another embodiment disclosed herein, the wound drainage therapy system further includes a control unit that is detachably connected with the actuator.

According to another embodiment disclosed herein, the collection bag has a negative-pressure buffer zone and two fluid collection zones that communicates with each other, the negative-pressure buffer zone is located between the two fluid collection zones and isolated from the two fluid collection zones, the two fluid collection zone are connected with the first connection port of the multiple-pipe integration module, the negative-pressure buffer zone is connected with the second and third connection ports of the multiple-pipe integration module, and the negative-pressure buffer zone has a fluid input port.

According to another embodiment disclosed herein, the negative-pressure buffer zone has a negative-pressure detection isolation section that is connected with the third connection port of the multiple-pipe integration module.

According to another embodiment disclosed herein, the negative-pressure buffer zone and the two fluid collection zones all have polyvinyl alcohol sheets inside thereof.

According to another embodiment disclosed herein, each of the two fluid collection zones has a ventilation hole and a waterproof ventilation sheet that is attached to the ventilation hole.

In accordance with the foregoing and other objectives of the present invention, a fluid collector unit of a wound drainage therapy system includes a multiple-pipe integration module and a collection bag. The multiple-pipe integration module includes first, second and third connection ports. The collection bag has a negative-pressure buffer zone and two fluid collection zones that communicates with each other, the negative-pressure buffer zone is located between the two fluid collection zones and isolated from the two fluid collection zones, the two fluid collection zone are connected with the first connection port of the multiple-pipe integration module, the negative-pressure buffer zone is connected with the second and third connection ports of the multiple-pipe integration module, and the negative-pressure buffer zone has a fluid input port.

According to another embodiment disclosed herein, the negative-pressure buffer zone has a negative-pressure detection isolation section that is connected with the third connection port of the multiple-pipe integration module.

According to another embodiment disclosed herein, the negative-pressure buffer zone and the two fluid collection zones all have polyvinyl alcohol sheets inside thereof.

According to another embodiment disclosed herein, the multiple-pipe integration module further includes fourth, fifth, sixth and seventh connection ports, and the first, fourth and seventh connection ports communicate with one another, the second and fifth connection ports communicate with each other, the third and sixth connection ports communicate with each other, the seventh connection port contains a backwater gate inside to stop flows reversed from the first or fourth connection ports.

According to another embodiment disclosed herein, the first, second, third, fourth, fifth, sixth and seventh connection ports are located on a common flat surface of the multiple-pipe integration module.

According to another embodiment disclosed herein, each of the two fluid collection zones has a ventilation hole and a waterproof ventilation sheet that is attached to the ventilation hole.

Thus, the wound drainage therapy system disclosed herein has modularized parts which can be easily assembled and disassembled with each other, the multiple-pipe integration module of which overcomes the piping entanglement problem, and the fluid collector unit is designed smaller to enable the wound drainage therapy system even more portable.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
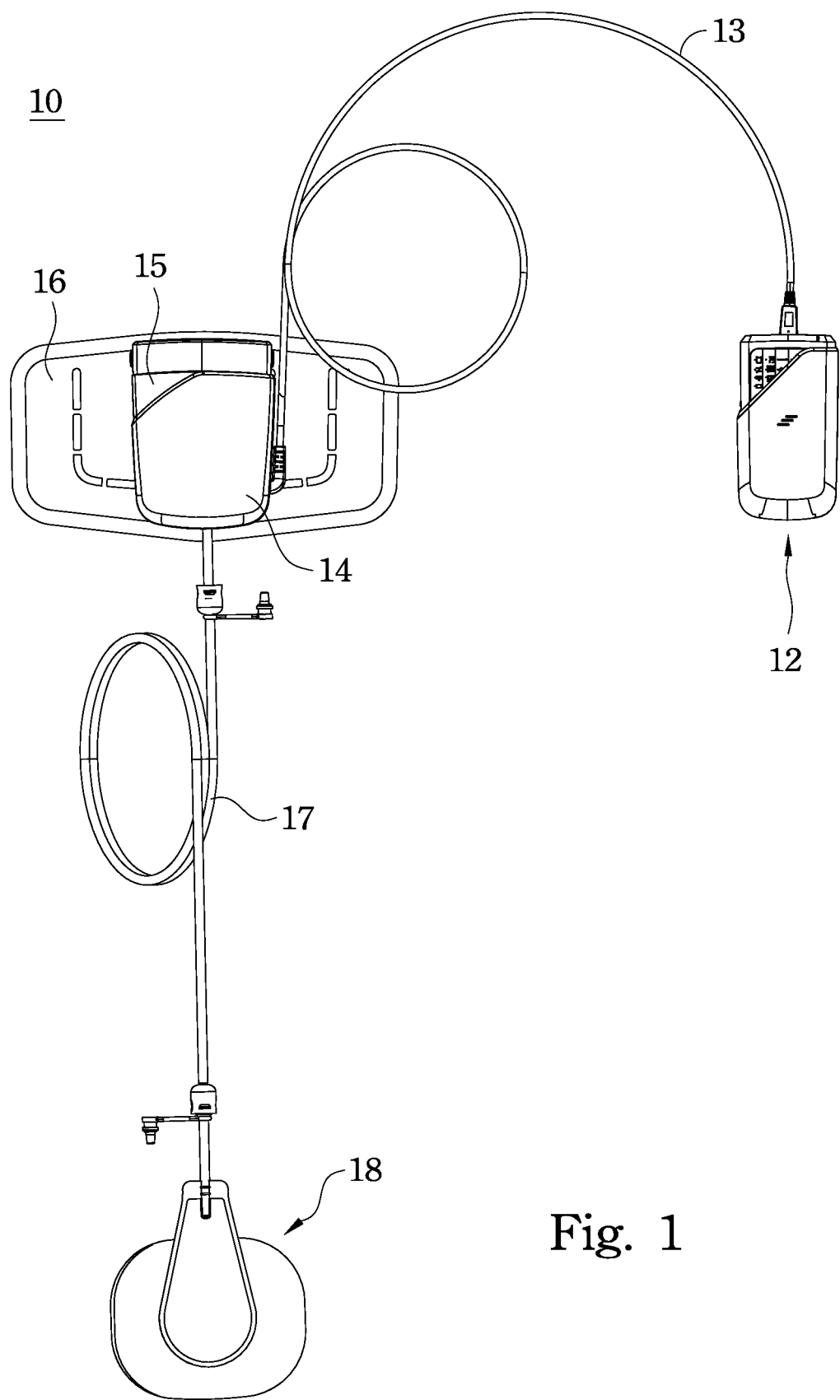
FIG. 1 illustrates an assembled view of a wound drainage therapy system according to an embodiment of this invention.

Reference will now be made in detail to the present preferred embodiments of the invention, examples of which are illustrated in the accompanying drawings. Wherever possible, the same reference numbers are used in the drawings and the description to refer to the same or like parts.

Figure 2:
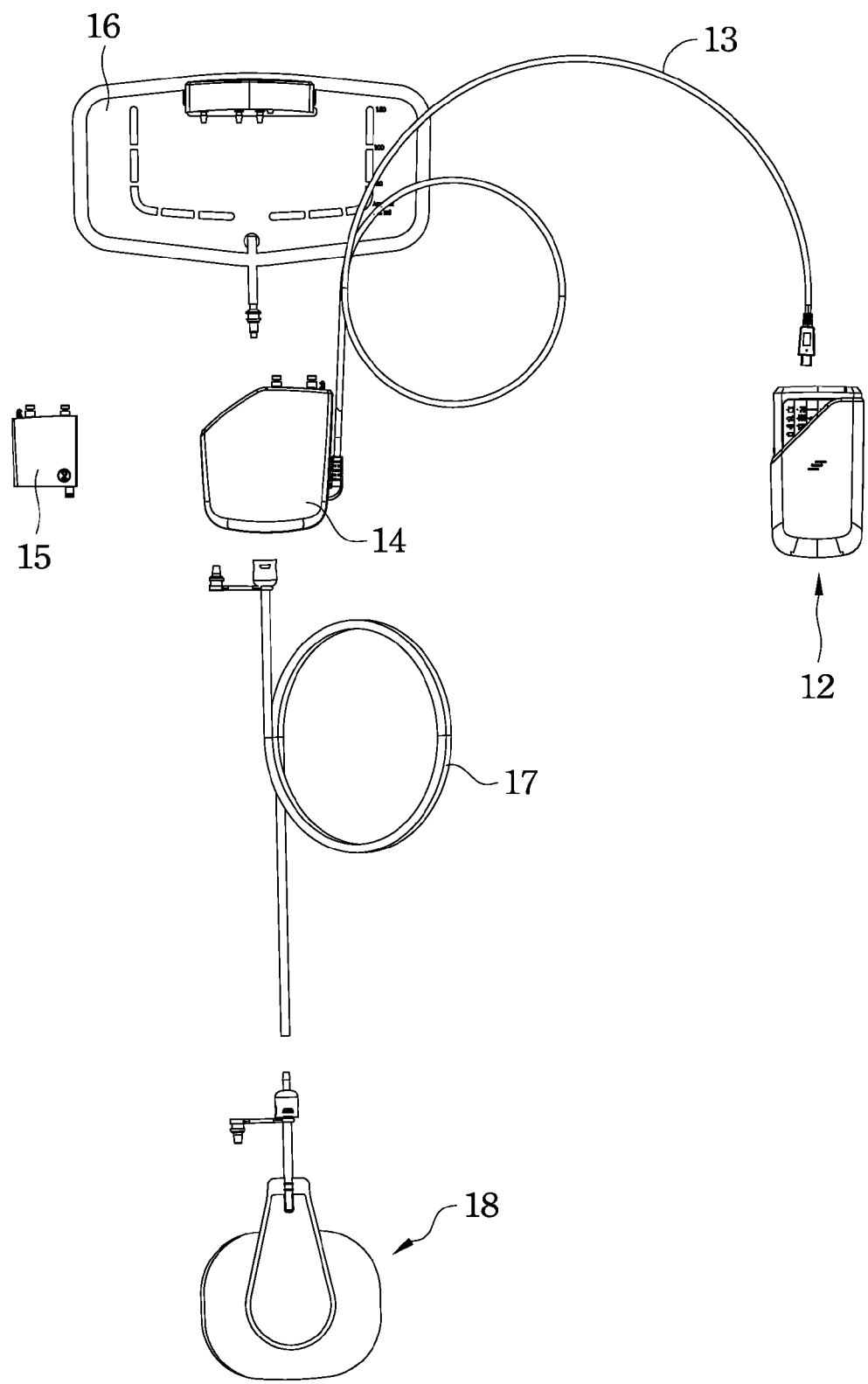
FIG. 2 illustrates an exploded view of the wound drainage therapy system in FIG. 1.

FIG. 1 illustrates an assembled view of a wound drainage therapy system according to an embodiment of this invention. FIG. 2 illustrates an exploded view of the wound drainage therapy system in FIG. 1. A modularized wound drainage therapy system 10 includes a control unit 12, an actuator 14, a vacuum driving unit 15, a fluid collector unit 16, a connection pipe 17 and a wound seal unit 18, wherein the fluid collector unit 16 and wound seal unit 18 are disposable parts. After the vacuum driving unit 15 is firstly used by a patient, the vacuum driving unit 15 would be infectious and thus should exclusively belong to the patient. The control unit 12 and actuator 14 are electronic parts of the wound drainage therapy system and can be repeatedly used in therapies for different patients. The control unit 12 is detachably connected with an electrical cable 13 of the actuator 14 such that the control unit 12 is able to control the operating of the actuator 14. The modularized wound drainage therapy system 10 not only make the fluid collector unit 16 smaller but also enable the electronic parts of high costs, e.g., the control unit 12 or actuator 14, to be repeatedly used in therapies for different patients, thereby reducing the using costs for the patients and preventing cross-infection among the patients.

Figure 3:
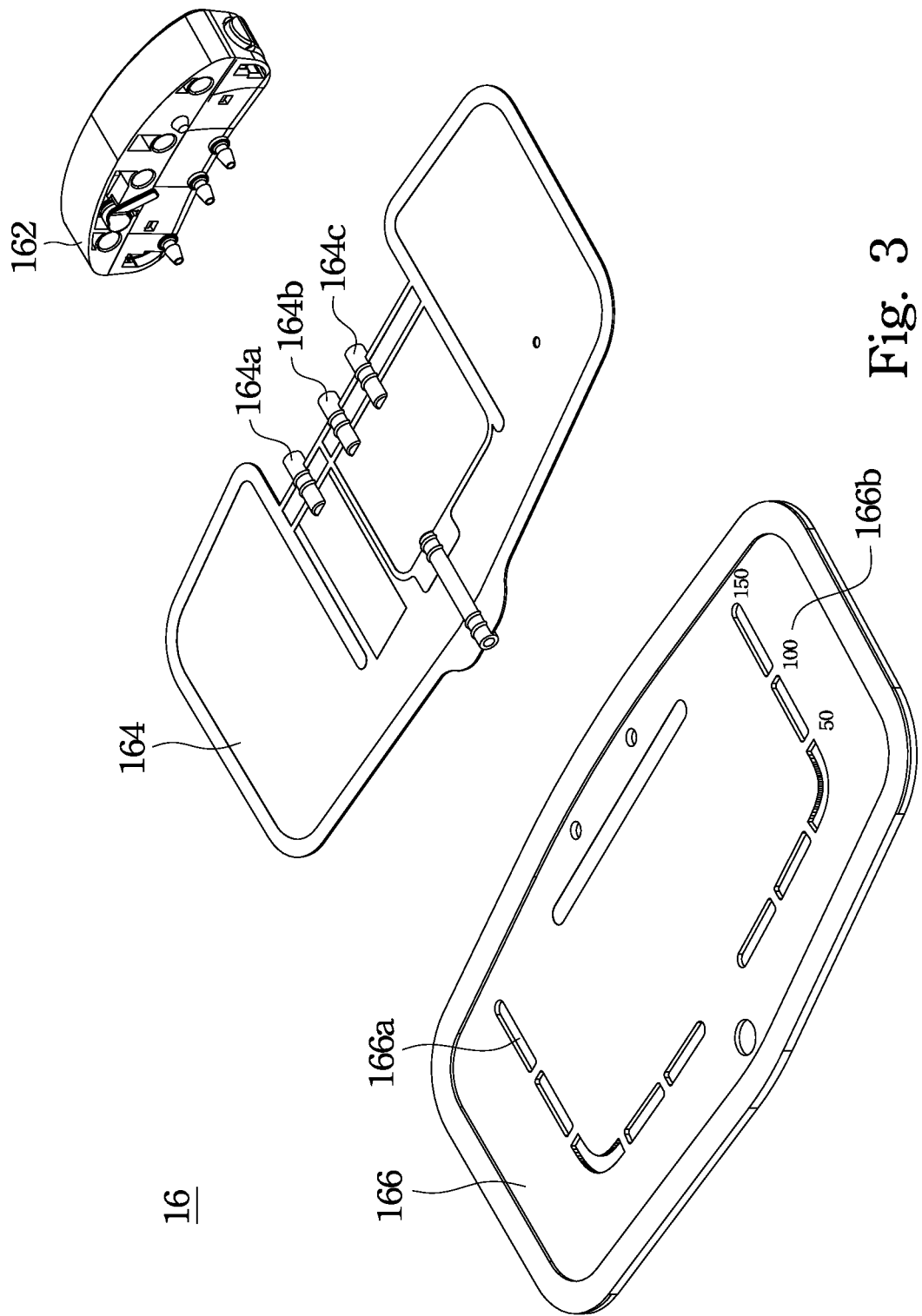
FIG. 3 illustrates an exploded view of a fluid collector unit in FIG. 1.

FIG. 3 illustrates an exploded view of a fluid collector unit in FIG. 1. The fluid collector unit 16 includes a multiple-pipe integration module 162, a collection bag 164 and an outer coat 166. The multiple-pipe integration module 162 is a single body for integrating all tubes connected to the collection bag 164 such that a wound drainage therapy system can be conveniently used and not bothered by piping entanglement. The collection bag 164 has three connection pipes (164a, 164b, 164c) that are connected to the connection ports of the multiple-pipe integration module 162 respectively. The outer coat 166 is used to enclose the collection bag 164 and has several openings 166a allowing a patient to check the fluid collection status of the collection bag via visual contacts. In addition, volume scales 166b are labeled around the opening 166a to assist estimating the fluid volume.

Figure 4:
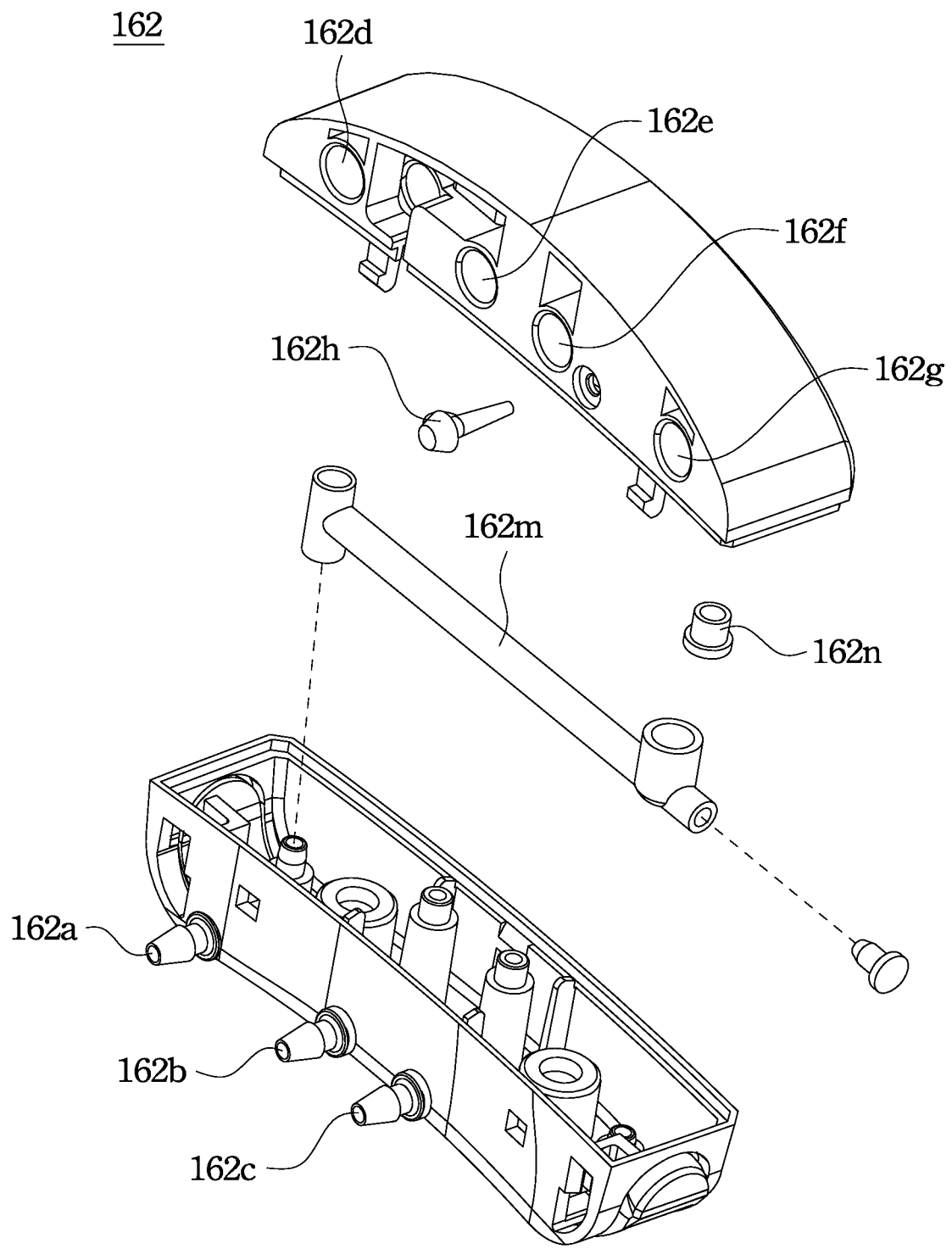
FIG. 4 illustrates an exploded view of a multiple-pipe integration module in FIG. 3.

FIG. 4 illustrates an exploded view of a multiple-pipe integration module in FIG. 3. The multiple-pipe integration module 162 includes an upper half housing and a lower half housing to assemble a complete one. The multiple-pipe integration module 162 includes a first row connection port group and a second row connection port group. The first row connection port group includes first, second and third connection ports (162a, 162b, 162c), and the second row connection port group includes fourth, fifth, sixth and seventh connection ports (162d, 162e, 162f, 162g). The first row connection port group and second row connection port group have the following connection relationship. The first, fourth and seventh connection ports (162a, 162d, 162g) communicate with one another by means of a three-way connection pipe 162m, the second and fifth connection ports (162b, 162e) communicate with each other, and the third and sixth connection ports (162c, 162f) communicate with each other. In addition, the seventh connection port 162g contains a backwater gate 162n inside thereof to stop flows reversed from the first or fourth connection ports (162a, 162d).

Figure 5:
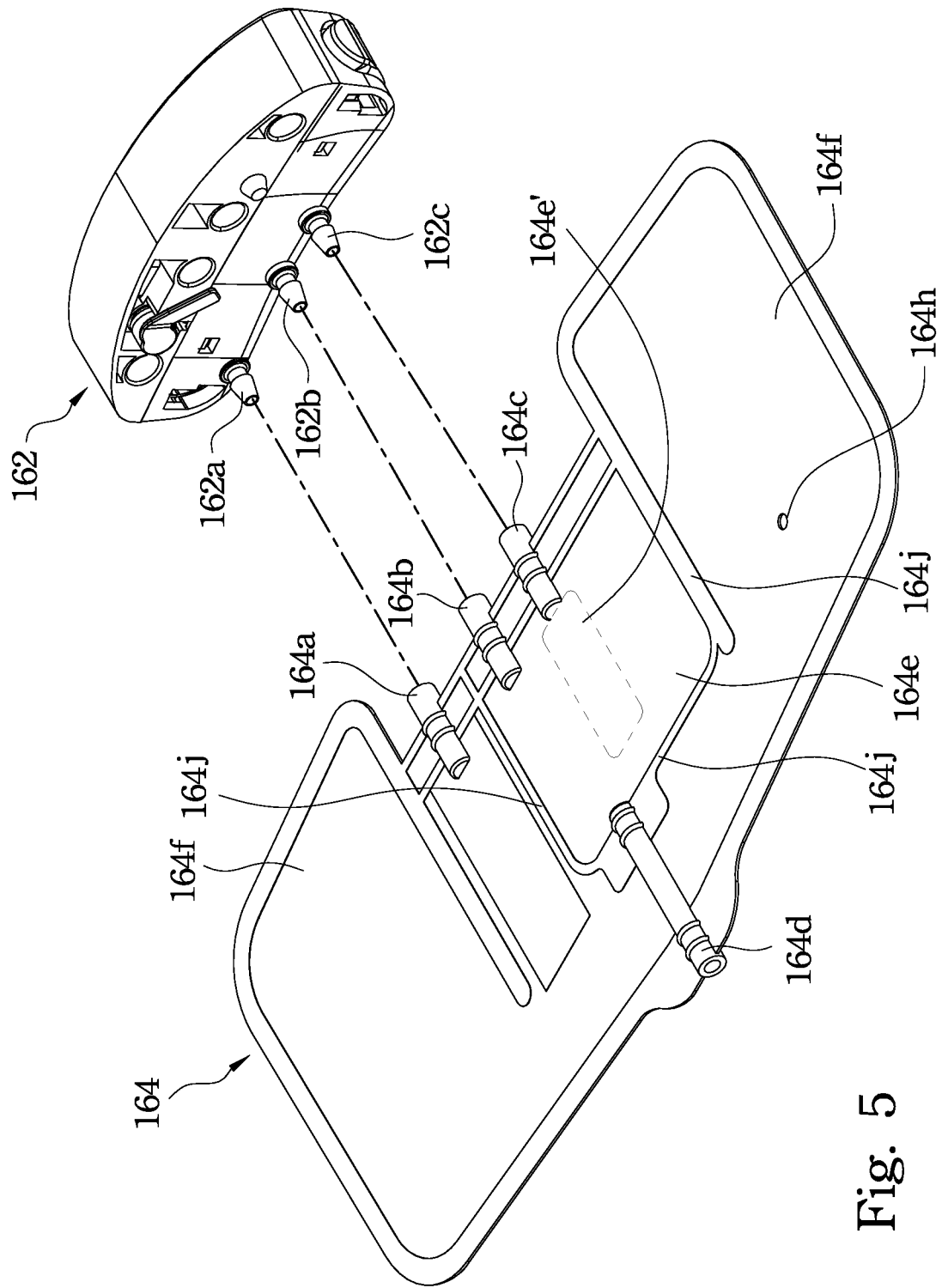
FIG. 5 illustrates an enlarged view of a multiple-pipe integration module and a collection bag in FIG. 3.

FIG. 5 illustrates an enlarged view of a multiple-pipe integration module and a collection bag in FIG. 3. The multiple-pipe integration module 162 includes first, second and third connection ports (162a, 162b, 162c) to be connected with the connection pipes (164a, 164b, 164c) of the collection bag 164 respectively. The collection bag 164 has a negative-pressure buffer zone 164e and two fluid collection zones 164f that communicate with each other. The negative-pressure buffer zone 164e is located between the two fluid collection zones 164f and isolated from the two fluid collection zones 164f, i.e., fluids (e.g., air or liquids) cannot cross over a border 164j between the negative-pressure buffer zone 164e and the two fluid collection zones 164f. The two fluid collection zones 164f is connected with the first connection port 162a of the multiple-pipe integration module 162 via the connection pipe 164a. The negative-pressure buffer zone 164e is connected with the second and third connection ports (162b, 162c) of the multiple-pipe integration module via the connection pipes (164b, 164c), and the negative-pressure buffer zone is equipped with a fluid input port 164d. The fluid input port 164d and the connection pipes (164b, 164c) are located at two opposite sides of the negative-pressure buffer zone 164e. The negative-pressure buffer zone 164e has a negative-pressure detection isolation section 164e' inside thereof to be connected with the third connection port 162c of the multiple-pipe integration module 162. The negative-pressure detection isolation section 164e' accommodates a negative-pressure detection head assembly so as to detect a negative-pressure status of the negative-pressure buffer zone 164e.

Figure 6:
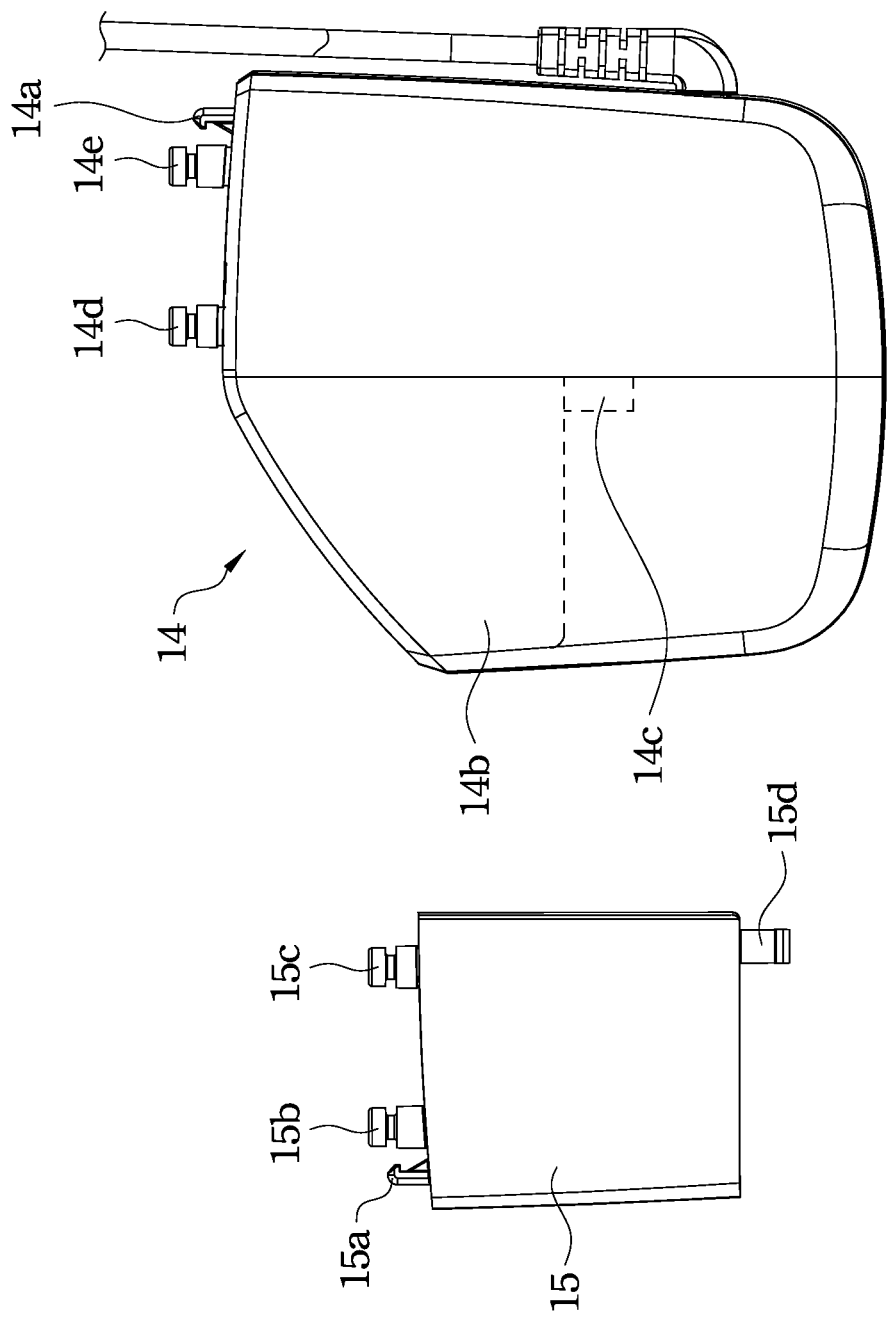
FIG. 6 illustrates an enlarged view of a vacuum driving unit and an actuator in FIG. 2.

FIG. 6 illustrates an enlarged view of a vacuum driving unit and an actuator in FIG. 2. The actuator 14 has a concave trough 14b to accommodate the vacuum driving unit 15, and the concave trough 14b has a fastening slot 14c. The vacuum driving unit 15 has a fastening hook 15d to detachably engage the fastening slot 14c of the actuator 14 such that the vacuum driving unit 15 can be secured within the concave trough 14b of the actuator 14. The vacuum generator 15 has two connection ports (15b, 15c). The actuator 14 has a connection port 14d of a negative pressure detector and a connection port 14e of a positive pressure detector.

Figure 7:
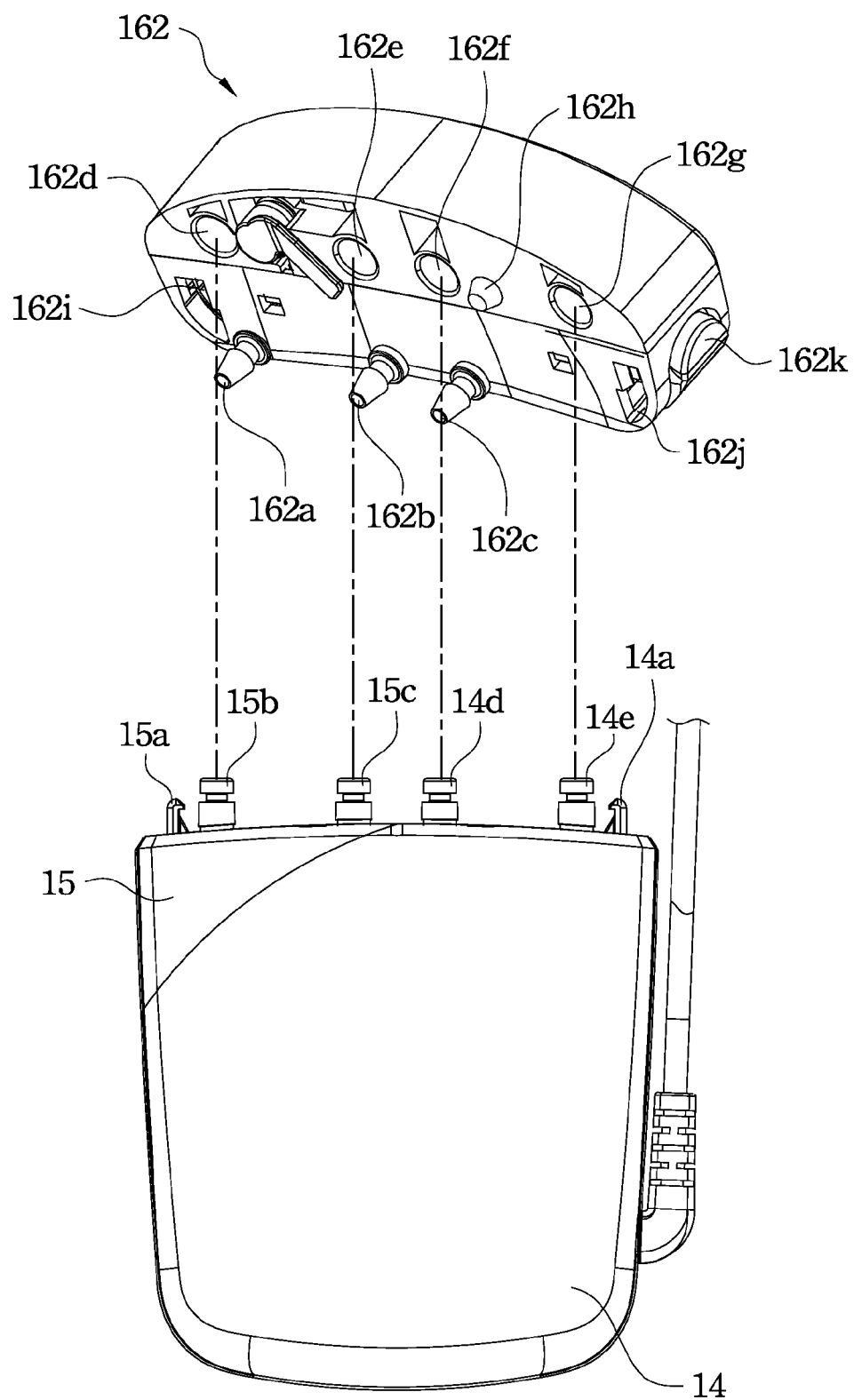
FIG. 7 illustrates a schematic view of the vacuum driving unit and the actuator connecting to the multiple-pipe integration module.

FIG. 7 illustrates a schematic view of the vacuum driving unit and the actuator connecting to the multiple-pipe integration module. After the vacuum driving unit 15 and the actuator 14 are assembled, the two connection ports (15b, 15c) of the vacuum generator, the connection port 14d of the negative pressure detector and the connection port 14e of the positive pressure detector are located on a common flat surface of a combined assembly of the vacuum driving unit 15 and the actuator 14. The first, second, third, fourth, fifth, sixth and seventh connection ports (162a, 162b, 162c, 162d, 162e, 162f, 162g) are located on a common flat surface of the multiple-pipe integration module 162. The flat surface of the multiple-pipe integration module 162 on which the first, second, third, fourth, fifth, sixth and seventh connection ports (162a, 162b, 162c, 162d, 162e, 162f, 162g) are located has two fastening slots (162i, 162j). The flat surface of the combined assembly of the vacuum driving unit 15 and the actuator 14 has two fastening hooks (14a, 15a) that detachably engage with the two fastening slots (162i, 162j) respectively so as to secure the multiple-pipe integration module 162 to the combined assembly of the vacuum driving unit 15 and the actuator 14.

When the multiple-pipe integration module 162 is fastened to the combined assembly of the vacuum driving unit 15 and the actuator 14, the two connection ports (15b, 15c) of the vacuum generator are detachably connected with the fourth and fifth connection ports (162d, 162e) of the multiple-pipe integration module 162 respectively, the connection port 14d of the negative pressure detector is detachably connected with the sixth connection port 162f of the multiple-pipe integration module 162, and the connection port 14e of the positive pressure detector is detachably connected with the seventh connection port 162g of the multiple-pipe integration module 162.

Referring to FIG. 5 and FIG. 7, when the connection port 14d of the negative pressure detector is connected with the sixth connection port 162f of the multiple-pipe integration module 162, the negative pressure detector can detect a negative-pressure status of the negative-pressure buffer zone 164e because the third and sixth connection ports (162c, 162f) communicate with each other.

Referring to FIG. 5 and FIG. 7, when the connection port 14e of the positive pressure detector is connected with the seventh connection port 162g of the multiple-pipe integration module 16, the positive pressure detector can detect a positive-pressure status of the two fluid collection zones 164f because the first, fourth and seventh connection ports (162a, 162d, 162g) communicate with one another. Because the seventh connection port 162g contains a backwater gate 162n (see FIG. 4), the reverse fluid flows, e.g. tissue fluids, from the first or fourth connection ports (162a, 162d) will not pass through the backwater gate 162n and damage the positive pressure detector.

When the multiple-pipe integration module 162 is desired to be detached from the combined assembly of the vacuum driving unit 15 and the actuator 14, a button 162k is pressed to disengage the two fastening hooks (14a, 15a) from the two fastening slots (162i, 162j) of the multiple-pipe integration module 162. After the multiple-pipe integration module 162 is detached from the combined assembly of the vacuum driving unit 15 and the actuator 14, a push member 162h does not contact a trigger member of the actuator 14 so as to stop a motor or detectors of the actuator 14 from operating.

Referring to both FIG. 5 and FIG. 7, when the vacuum driving unit 15 is operating to generate a negative pressure, the fluids within the negative-pressure buffer zone 164e is drained via the connection pipe 164b and directed into the two fluid collection zones 164f via the connection pipe 164a such that the negative-pressure level of the negative-pressure buffer zone 164e is increased so as to suck more fluids via the fluid input port 164d. When the fluids within the negative-pressure buffer zone 164e is totally drained out, the vacuum driving unit 15 stops operating.

Figure 8:
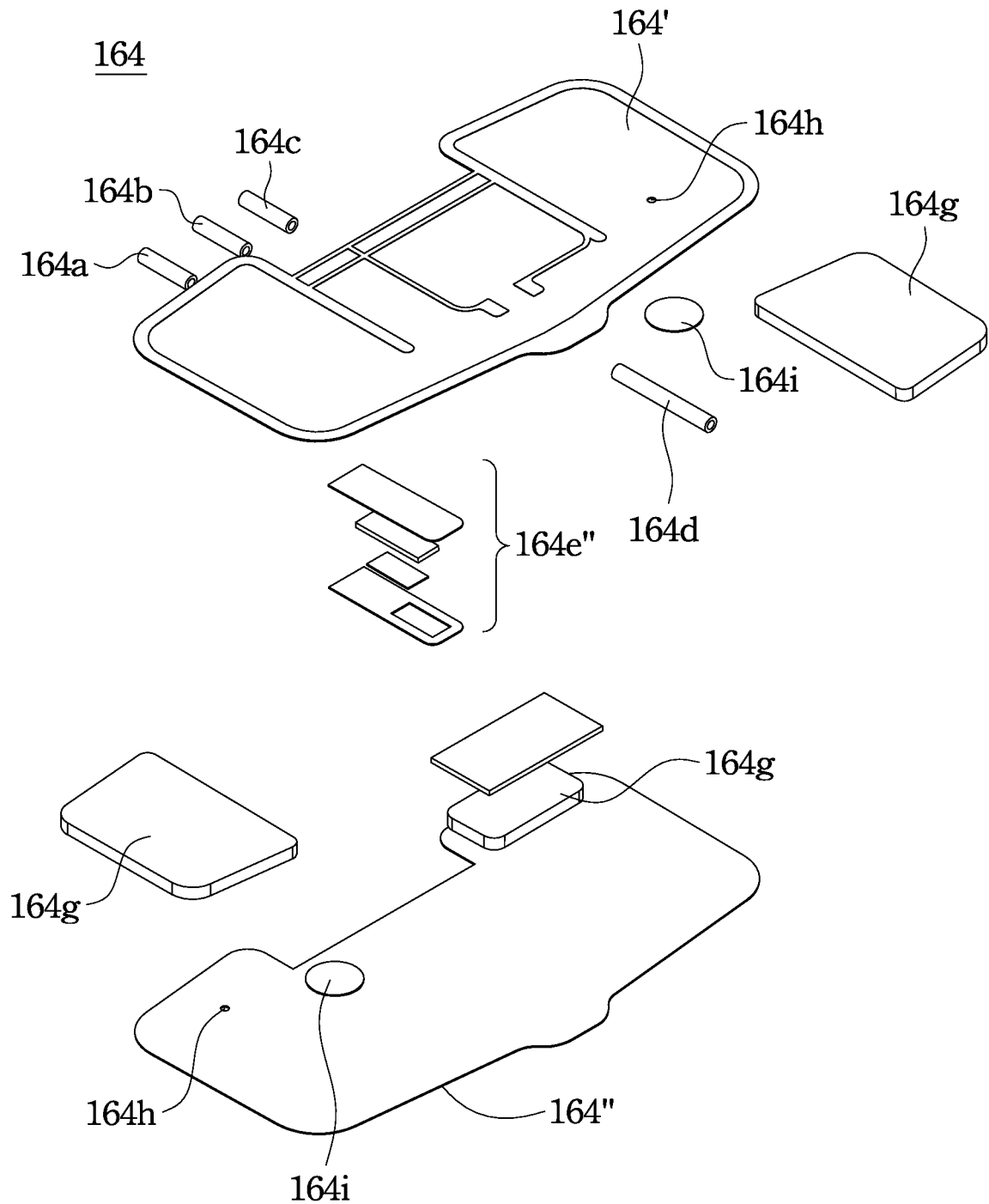
FIG. 8 illustrates an exploded view of the collection bag in FIG. 5.

Referring to both FIG. 5 and FIG. 8, wherein FIG. 8 illustrates an exploded view of the collection bag in FIG. 5. The collection bag 164 basically includes an upper sheet 164' and a lower sheet 164" that are attached to sandwich the remaining components illustrated in the FIG. 8. The negative-pressure buffer zone 164e and two fluid collection zones 164f all have polyvinyl alcohol sheets 164g inside thereof. Each polyvinyl alcohol sheet 164g is used to absorb the fluids within the negative-pressure buffer zone or the fluid collection zone and thus maintains a workable air ventilation path. Each of the two fluid collection zones 164f has a ventilation hole 164h and a waterproof ventilation sheet 164i that is attached to the ventilation hole 164h such that excessive air within the two fluid collection zones 164*f* can be exhausted out through the ventilation hole 164*h*. The negative-pressure detection isolation section 164*e'* accommodates a negative-pressure detection head assembly 164*e"* so as to detect a negative-pressure status of the negative-pressure buffer zone 164*e*.

Figure 9:
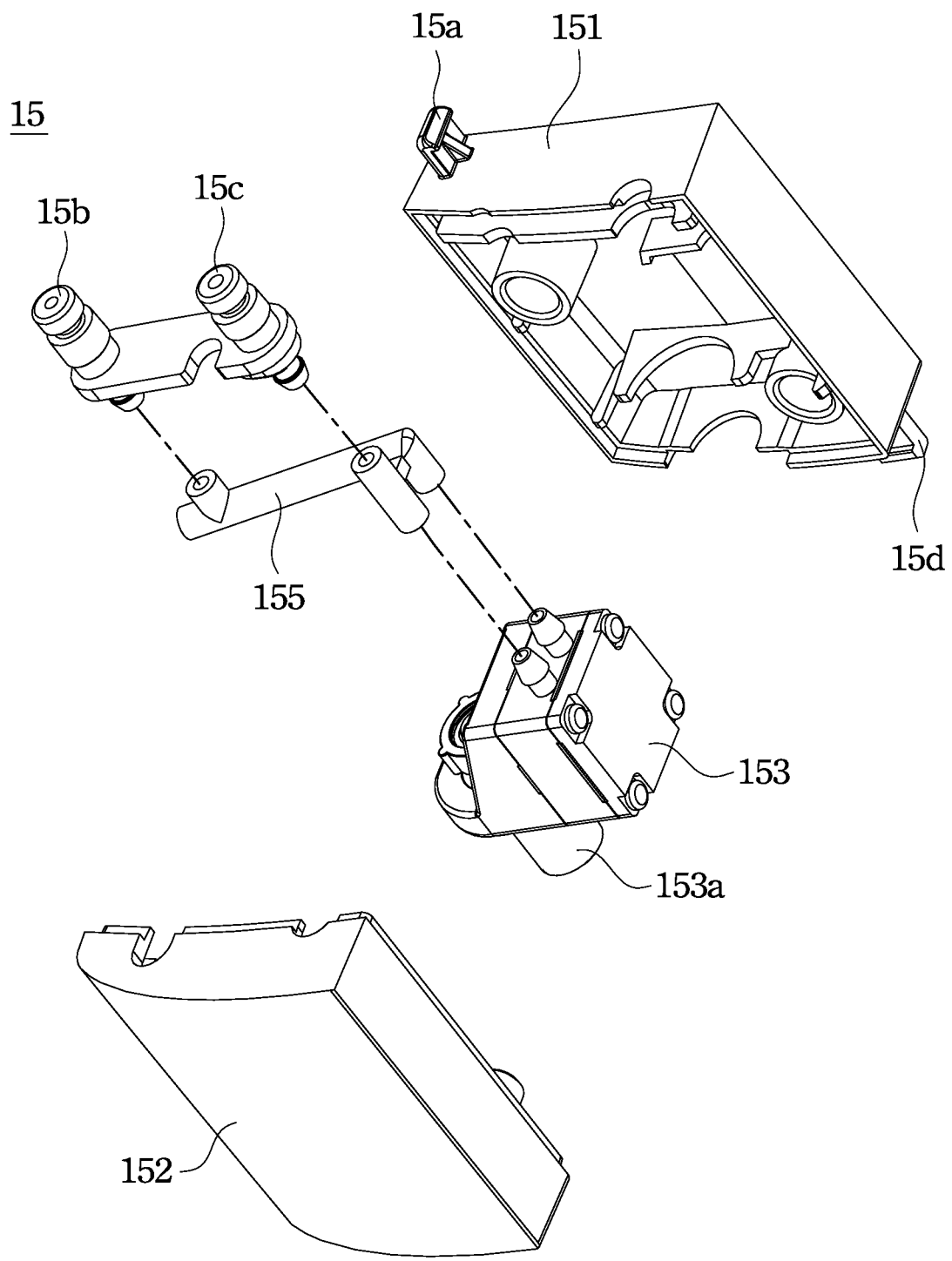
FIG. 9 illustrates an exploded view of the vacuum driving unit in FIG. 6.

FIG. 9 illustrates an exploded view of the vacuum driving unit in FIG. 6. The vacuum driving unit 15 contains a vacuum generator 153 and two half housings (151, 152). The two half housings (151, 152) are assembled to enclose the vacuum generator 153. The vacuum generator 153 has a rotation shaft 153*a* that is detachably connected with the motor of the actuator 14 such that the vacuum generator 153 can be driven to generate a negative-pressure. The vacuum generator 153 is connected with the upper two connection ports (15*b*, 15*c*) via the connection pipe 155.

Figure 10:
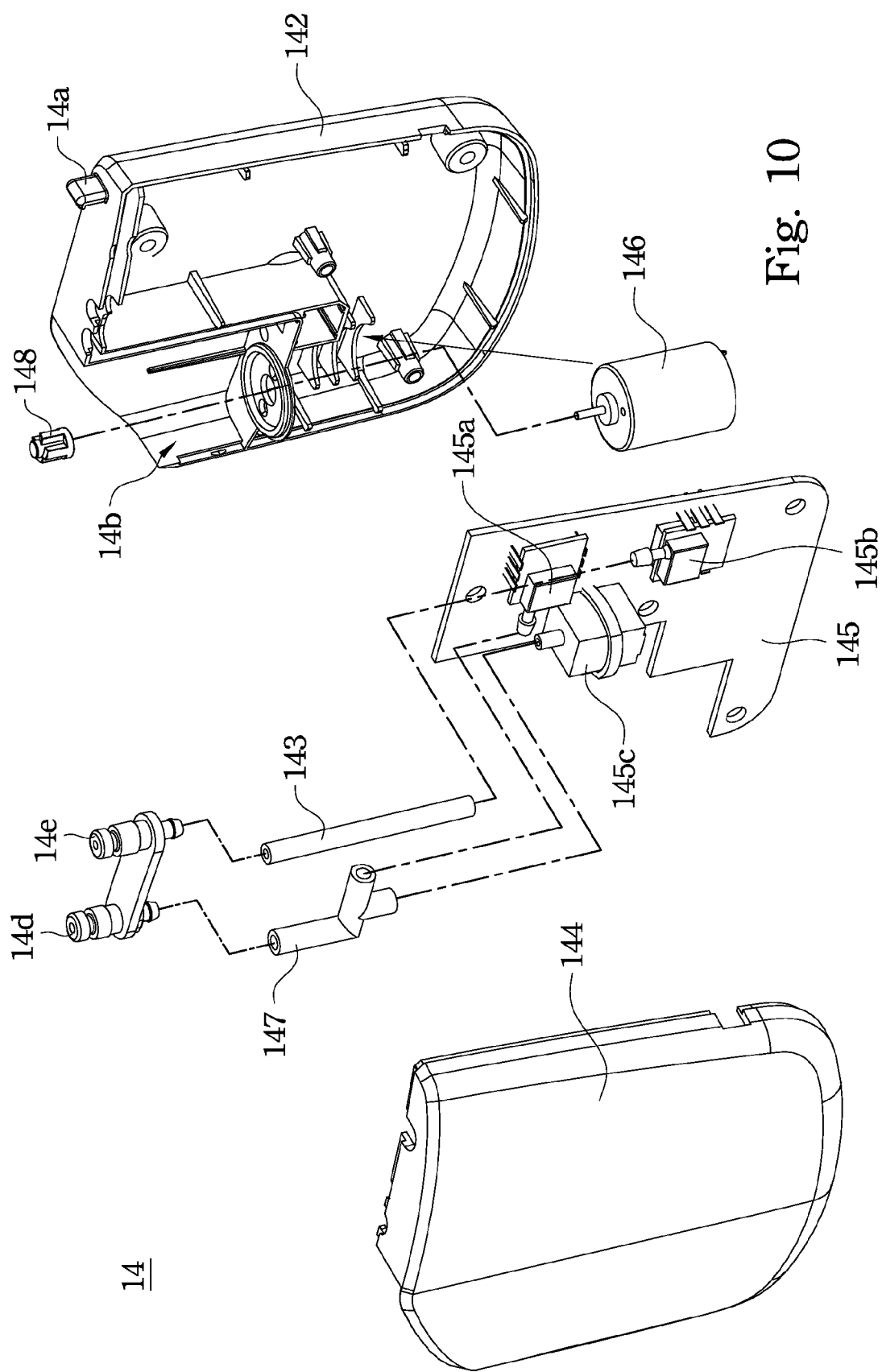
FIG. 10 illustrates an exploded view of the actuator in FIG. 6.

FIG. 10 illustrates an exploded view of the actuator in FIG. 6. The actuator 14 contains a motor 146, a negative pressure detector 145*a* and a positive pressure detector 145*b*. The actuator 14 has two half housings (142, 144). When the two half housings (142, 144) are assembled, the motor, the negative pressure detector and positive pressure detector are sandwiched therebetween. The motor 146 is fastened to the place to which an arrow is directed and its rotation shaft is connected to a shaft gear 148. When the vacuum driving unit 15 is assembled within the concave trough 14*b* of the actuator 14, the shaft gear 148 is used to drive the vacuum generator 153 to generate a negative pressure. The negative pressure detector 145*a* and positive pressure detector 145*b* are both mounted on a circuit board 145. A three-way connection pipe 147 has an upper port connected to the connection port 14*d* and two lower ports connected to the negative pressure detector 145*a* and a pressure relief valve 145*c*. A connection pipe 143 has an upper port connected to the connection port 14*e* and a lower port connected to the positive pressure detector 145*b*.

Figure 11:
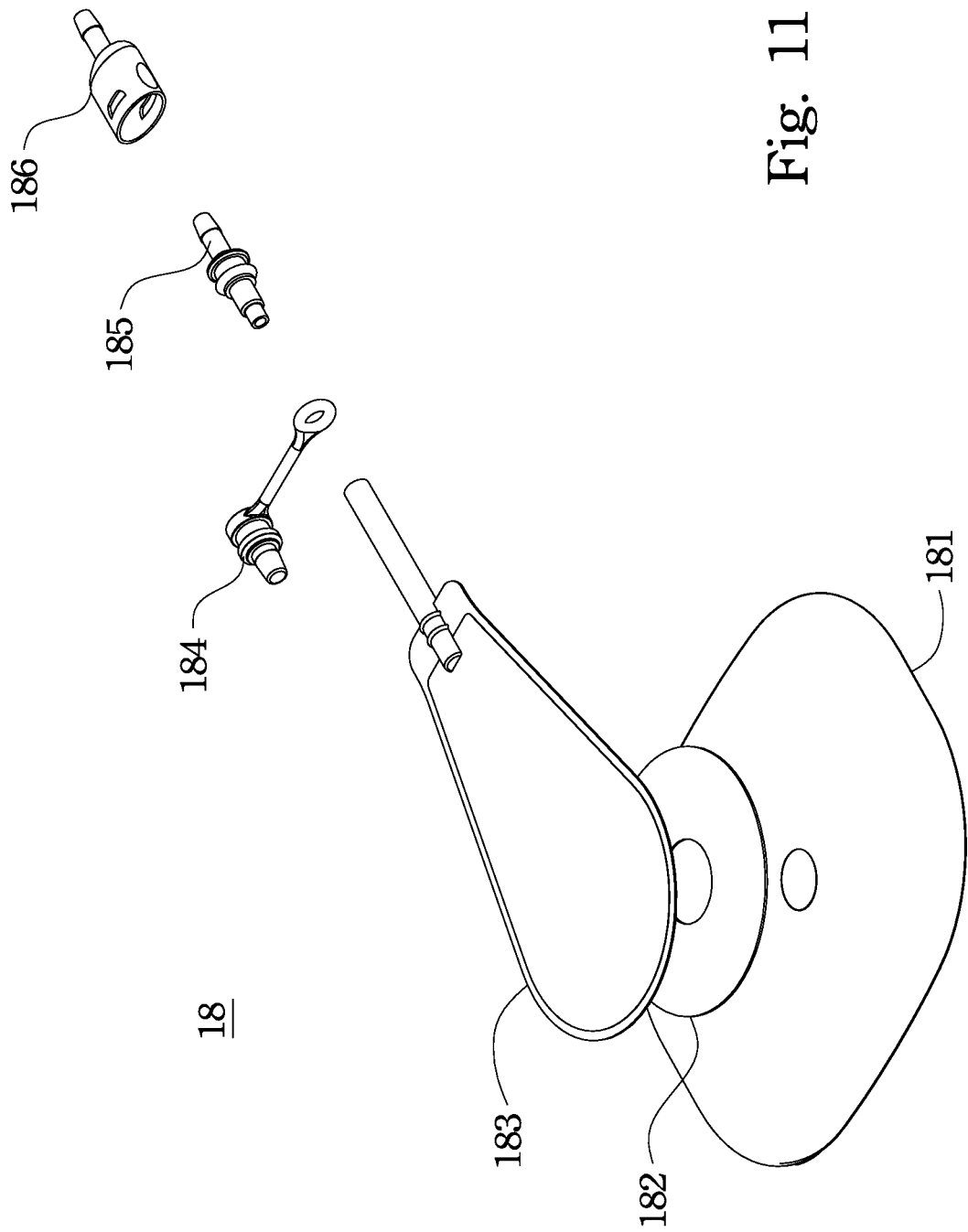
FIG. 11 illustrates an exploded view of a wound seal unit in FIG. 2.

FIG. 11 illustrates an exploded view of a wound seal unit in FIG. 2. The wound seal unit 18 is attached to a wound such that the wound drainage therapy system can suck the tissue fluid of the wound through the wound seal unit 18. The wound seal unit 18 includes a tape 181, a filter sheet 182 and a bag 183 that are laminated together in accordance with the relative position illustrated in FIG. 11. The tape 181 is affixed to the skin around the wound such that the wound seal unit 18 can be attached to the wound. The wound seal unit 18 further has a male connecter 185, a female connecter 186 and a connecter hat 184*a*. The male connecter 185 and the female connecter 186 can be detachably connected with each other. After the male connecter 185 is detached from the female connecter 186, the connecter hat 184 can be used to shield the male connector 185 to prevent the external contamination.

According to the above-discussed embodiments, the wound drainage therapy system disclosed herein has modularized parts which can be easily assembled and disassembled with each other, the multiple-pipe integration module of which overcomes the piping entanglement problem, and the fluid collector unit is designed smaller to enable the wound drainage therapy system even more portable.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A wound drainage therapy system comprising:
a wound seal unit being attached to a wound;
a fluid collector unit being detachably connected with the wound seal unit, the fluid collector unit having a multiple-pipe integration module and a collection bag, wherein the multiple-pipe integration module has a first row connection port group that is connected with the collection bag, the multiple-pipe integration module further has a second row connection port group, the first row connection port group communicates with the second row connection port group;
a vacuum driving unit having a vacuum generator inside thereof, two connection ports of the vacuum generator being detachably connected with two connection ports of the second row connection port group respectively; and
an actuator having a motor, a negative pressure detector and a positive pressure detector inside thereof, wherein the motor is used to drive the vacuum generator to operate and the motor is detachably connected with the vacuum generator, a connection port of the negative pressure detector and a connection port of the positive pressure detector are detachably connected with another two connection ports of the second row connection port group respectively.

2. The wound drainage therapy system of claim 1, wherein the first row connection port group comprises first, second and third connection ports, and the second row connection port group comprises fourth, fifth, sixth and seventh connection ports.

3. The wound drainage therapy system of claim 2, wherein the two connection ports of the vacuum generator are connected with the fourth and fifth connection ports respectively, the connection port of the positive pressure detector is connected with the seventh connection port, and the connection port of the negative pressure detector is connected with the sixth connection port.

4. The wound drainage therapy system of claim 2, wherein the first, fourth and seventh connection ports communicate with one another, the second and fifth connection ports communicate with each other, the third and sixth connection ports communicate with each other, and the seventh connection port contains a backwater gate inside to stop flows reversed from the first or fourth connection ports.

5. The wound drainage therapy system of claim 2, wherein when the vacuum driving unit is assembled to the actuator, the two connection ports of the vacuum generator, the connection port of the negative pressure detector and the connection port of the positive pressure detector are located on a common flat surface of a combined assembly of the vacuum driving unit and the actuator.

6. The wound drainage therapy system of claim 5, wherein the first, second, third, fourth, fifth, sixth and seventh connection ports are located on a common flat surface of the multiple-pipe integration module.

7. The wound drainage therapy system of claim 6, wherein the flat surface of the multiple-pipe integration module has two fastening slots.

8. The wound drainage therapy system of claim 7, wherein the flat surface of the combined assembly of the vacuum driving unit and the actuator has two fastening hooks that detachably engage with the two fastening slots respectively.

9. The wound drainage therapy system of claim 1, wherein the actuator has a concave trough to accommodate the vacuum driving unit and the concave trough has a fastening slot.

10. The wound drainage therapy system of claim 9, wherein the vacuum driving unit has a fastening hook that detachably engages with the fastening slot within the concave trough such that the vacuum driving unit is secured within the concave trough of the actuator.

11. The wound drainage therapy system of claim 1, further comprising a control unit that is detachably connected with the actuator.

12. The wound drainage therapy system of claim 4, wherein the collection bag has a negative-pressure buffer zone and two fluid collection zones that communicate with each other, the negative-pressure buffer zone is located between the two fluid collection zones and isolated from the two fluid collection zones, the two fluid collection zone are connected with the first connection port of the multiple-pipe integration module, the negative-pressure buffer zone is connected with the second and third connection ports of the multiple-pipe integration module, and the negative-pressure buffer zone has a fluid input port.

13. The wound drainage therapy system of claim 12, wherein the negative-pressure buffer zone has a negative-pressure detection isolation section that is connected with the third connection port of the multiple-pipe integration module.

14. The wound drainage therapy system of claim 12, wherein the negative-pressure buffer zone and the two fluid collection zones all have polyvinyl alcohol sheets inside thereof.

15. The wound drainage therapy system of claim 12, wherein each of the two fluid collection zones has a ventilation hole and a waterproof ventilation sheet that is attached to the ventilation hole.

* * * * *